US009174015B2

(12) United States Patent
Stevens et al.

(10) Patent No.: US 9,174,015 B2
(45) Date of Patent: Nov. 3, 2015

(54) MANAGING AN ACTIVE STRAP SYSTEM FOR A FACE MASK

(71) Applicant: INTERNATIONAL BUSINESS MACHINES CORPORATION, Armonk, NY (US)

(72) Inventors: Mark B. Stevens, Austin, TX (US); John D. Wilson, Houston, TX (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/093,030

(22) Filed: Nov. 28, 2013

(65) Prior Publication Data
US 2014/0090646 A1 Apr. 3, 2014

Related U.S. Application Data

(63) Continuation of application No. 13/297,550, filed on Nov. 16, 2011.

(51) Int. Cl.
A61M 16/06 (2006.01)
A61M 16/00 (2006.01)
A61M 16/08 (2006.01)

(52) U.S. Cl.
CPC ....... *A61M 16/0683* (2013.01); *A61M 16/0051* (2013.01); *A61M 16/0057* (2013.01); *A61M 16/0875* (2013.01); *A61M 16/06* (2013.01); *A61M 2016/0027* (2013.01); *A61M 2205/15* (2013.01); *A61M 2205/332* (2013.01); *A61M 2205/3553* (2013.01); *A61M 2205/3561* (2013.01); *A61M 2205/3584* (2013.01); *A61M 2205/3592* (2013.01)

(58) Field of Classification Search
CPC .................... A61M 16/0683; A61M 16/0694; A62B 18/084
USPC ........................... 128/205.25, 206.21–207.13
See application file for complete search history.

(56) References Cited

U.S. PATENT DOCUMENTS

| 3,792,702 | A | * | 2/1974 | Delest ....................... 128/207.11 |
| 5,623,923 | A | * | 4/1997 | Bertheau et al. ......... 128/207.11 |
| 6,039,045 | A | * | 3/2000 | Bertheau et al. ......... 128/207.11 |
| 6,676,613 | B2 | | 1/2004 | Cantrell et al. |
| 6,749,548 | B2 | | 6/2004 | Hoffman |

(Continued)

FOREIGN PATENT DOCUMENTS

| EP | 1981459 B1 | 10/2008 |
| WO | 2004041342 A1 | 5/2004 |
| WO | 2011048518 A1 | 4/2011 |

OTHER PUBLICATIONS

"A Nasal Mask that Changes the Game", Philips, found on the World Wide Web at http://www.healthcare.philips.com/main/homehealth/sleep/easylife/default.wpd.
"Pressure Sensor for Sleep Apnea Mask", Silicon Microstructures, found on the World Wide Web at http://www.si-micro.com/applications/medical/sleep-apnea/.
"Hybrid Universal Interface", DeVilbiss Healthcase, found on the World Wide Web at http://www.directhomemedical.com/pdf/hybrid-mask-broch.pdf.

(Continued)

Primary Examiner — Valerie L Skorupa
(74) Attorney, Agent, or Firm — Paul S. Drake

(57) ABSTRACT

A method for managing a set of active straps for a positive airway pressure (PAP) mask including detecting a pressure value with a pressure sensor, analyzing the pressure value with a processor for identifying an adjustment of the set of active straps, and performing the identified adjustment with the set of active straps.

10 Claims, 5 Drawing Sheets

(56) References Cited

U.S. PATENT DOCUMENTS

| | | |
|---|---|---|
| 7,575,005 B2 | 8/2009 | Mumford et al. |
| 8,364,220 B2 * | 1/2013 | Sandmore .................... 600/323 |
| 2002/0056452 A1 * | 5/2002 | Brewer et al. ............ 128/202.22 |
| 2006/0118117 A1 * | 6/2006 | Berthon-Jones et al. 128/206.21 |
| 2008/0083412 A1 | 4/2008 | Henry et al. |
| 2008/0083414 A1 * | 4/2008 | Messerges .................... 128/920 |
| 2008/0264422 A1 | 10/2008 | Fishman |
| 2011/0209708 A1 * | 9/2011 | Rapoport ................. 128/205.25 |

OTHER PUBLICATIONS

"A Nasal Mask that Changes the Game", Philips, found on the World Wide Web at http://www.healthcare.philips.com/main/homehealth/sleep/easylife/default.wpd, 2004 /VS/.

"Pressure Sensor for Sleep Apnea Mask", Silicon Microstructures, found on the World Wide Web at http://www.si-micro.com/applications/medical/sleep-apnea/, 2010 /VS/.

"Hybrid Universal Interface", DeVilbiss Healthcase, found on the World Wide Web at http://www.directhomemedical.com/pdf/hybrid-mask-broch.pdf, 2008 /VS/.

* cited by examiner

MANAGING AN ACTIVE STRAP SYSTEM FOR A FACE MASK

This application is a continuation of application Ser. No. 13/297,550 filed Nov. 16, 2011 entitled "MANAGING AN ACTIVE STRAP SYSTEM FOR A FACE MASK", the disclosure of which is incorporated in its entirety herein by reference.

BACKGROUND

1. Technical Field

The present invention relates generally to an active strap for a face mask, and in particular, to a computer implemented method for an active strap tensioning system for a positive airway pressure mask.

2. Description of Related Art

Sleep apnea is a sleep disorder characterized by abnormal pauses in breathing or instances of abnormally low breathing. Each pause in breathing, called an apnea, can last from a few seconds to minutes and may occur many times each hour. Untreated or poorly treated sleep apnea can cause fatigue and result in serious medical conditions over time such as high blood pressure, heart attacks, arrhythmias and even automobile crashes.

Typical treatment for sleep apnea is for the patient to use a positive airway pressure (PAP) system which increases air pressure in the patient's airway and allows the patient to sleep without apnea events. However, this treatment of sleep apnea is problematic and patients often cease using the PAP system due to these difficulties. One of the main sources of issues is the PAP mask. The mask needs to be sealed to prevent air leaks while not being so tight as to generate pressure sores and irritation around the mask. Because every patient's face is different, various mask geometries may be used, including customizations, yet these issues often persist. These issues are aggravated by the patient moving into various sleep positions or by the patient rubbing the face and mask during the night.

SUMMARY

The illustrative embodiments provide a method for managing a set of active straps for a positive airway pressure (PAP) mask including detecting a pressure value with a pressure sensor, analyzing the pressure value with a processor for identifying an adjustment of the set of active straps, and performing the identified adjustment with the set of active straps.

BRIEF DESCRIPTION OF THE SEVERAL VIEWS OF THE DRAWINGS

The novel features believed characteristic of the invention are set forth in the appended claims. The invention itself, further objectives and advantages thereof, as well as a preferred mode of use, will best be understood by reference to the following detailed description of illustrative embodiments when read in conjunction with the accompanying drawings, wherein:

DETAILED DESCRIPTION

Steps may be taken to provide an active strap tensioning system for a continuous pressure mask. These steps may be taken as will be explained with reference to the various embodiments below.

Figure 1:
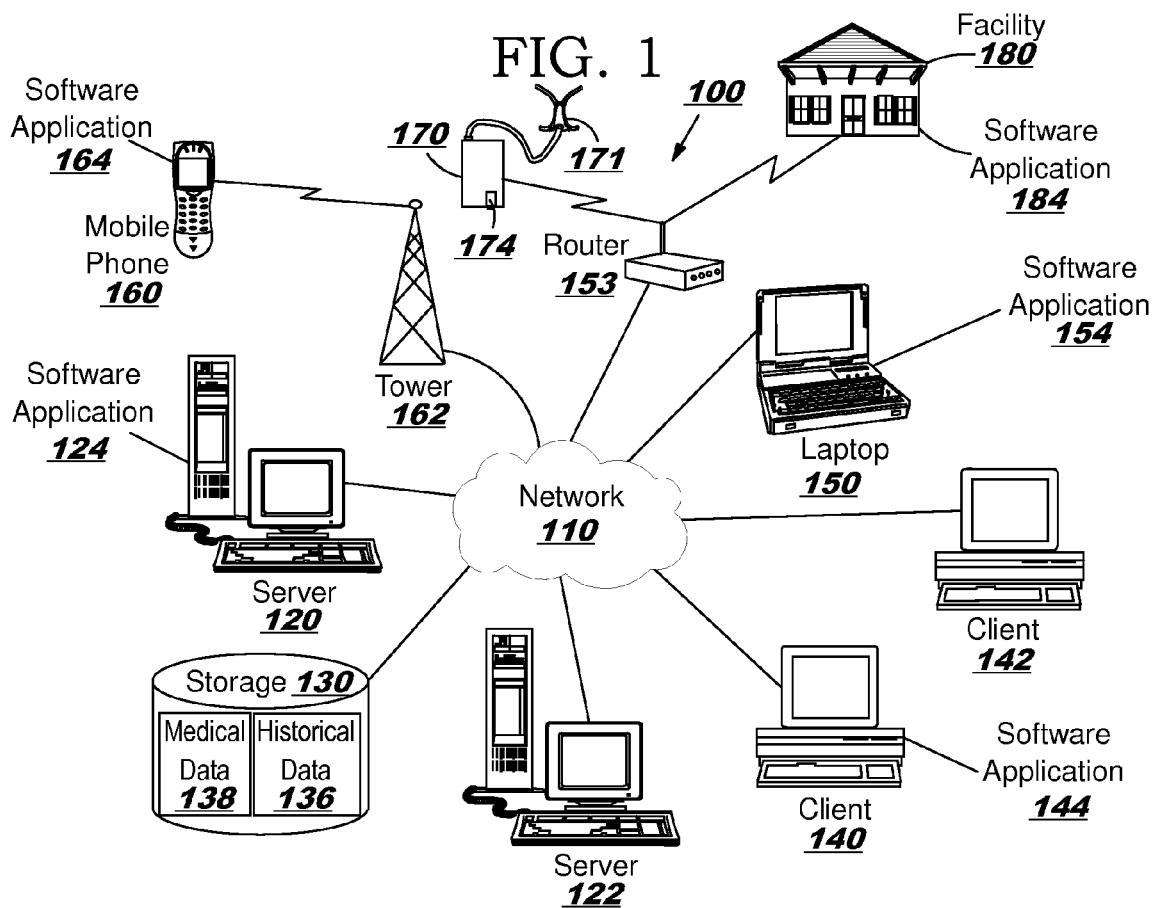
FIG. 1 is a block diagram of a network of data processing systems in which various embodiments may be implemented.

FIG. 1 is a block diagram of a network of data processing systems in which various embodiments may be implemented. Data processing environment 100 is a network of data processing systems also known as computers or computer devices in which the embodiments may be implemented. Software applications may execute on any computer or other type of data processing system in data processing environment 100. Data processing environment 100 includes network 110. Network 110 is the medium used to provide communications links between various devices and computers connected together within data processing environment 100. Network 110 may include connections such as wire, wireless communication links, or fiber optic cables.

Servers 120 and 122 and clients 140 and 142 are coupled to network 110 along with storage unit 130. In addition, laptop 150, mask pump 170 with mask 171, and facility 180 (such as a home or business) are coupled to network 110 including wirelessly such as through a network router 153. A mobile phone 160 is coupled to network 110 through a mobile phone tower 162. Data processing systems, such as server 120 and 122, client 140 and 142, laptop 150, mobile phone 160, mask pump 170, facility 180 contain a processor, data and have software applications including software tools executing thereon. Other types of data processing systems such as personal digital assistants (PDAs), smartphones, tablets and netbooks may be coupled to network 110.

Server 120 may include software application 124 such as for managing an environmental control system for the various computer devices or other software applications in accordance with embodiments described herein. Storage 130 may contain a content source such historical data 136 for maintaining historical performance data from mask pump 170, medical data regarding the patient using mask 171, or other content for sharing among various computer or other data processing devices. Client 140 may include software application 144. Laptop 150 and mobile phone 160 may also include software applications 154 and 164. Mask pump 170 and facility 180 may include software applications 174 and 184. Other types of data processing systems coupled to network 110 may also include software applications. Software applications could include a web browser, email, or other software application that can process sensor and maintenance information of an environmental control unit or other type of information to be processed.

Servers 120 and 122, storage unit 130, clients 140 and 142, laptop 150, mobile phone 160, mask pump 170 and facility 180 and other data processing devices may couple to network 102 using wired connections, wireless communication protocols, or other suitable data connectivity. Clients 140 and 142 may be, for example, personal computers or network computers.

In the depicted example, server 120 may provide data, such as boot files, operating system images, and applications to clients 140 and 142 and laptop 150. Clients 140 and 142 and laptop 150 may be clients to server 120 in this example. Clients 140 and 142, laptop 150, mobile phone 160, mask pump 170 and facility 180 or some combination thereof, may include their own data, boot files, operating system images, and applications. Data processing environment 100 may include additional servers, clients, and other devices that are not shown.

In the depicted example, data processing environment 100 may be the Internet. Network 110 may represent a collection of networks and gateways that use the Transmission Control Protocol/Internet Protocol (TCP/IP) and other protocols to communicate with one another. At the heart of the Internet is a backbone of data communication links between major nodes or host computers, including thousands of commercial, governmental, educational, and other computer systems that route data and messages. Of course, data processing environment 100 also may be implemented as a number of different types of networks, such as for example, an intranet, a local area network (LAN), or a wide area network (WAN). FIG. 1 is intended as an example, and not as an architectural limitation for the different illustrative embodiments.

Among other uses, data processing environment 100 may be used for implementing a client server environment in which the embodiments may be implemented. A client server environment enables software applications and data to be distributed across a network such that an application functions by using the interactivity between a client data processing system and a server data processing system. Data processing environment 100 may also employ a service oriented architecture where interoperable software components distributed across a network may be packaged together as coherent business applications.

Figure 2:
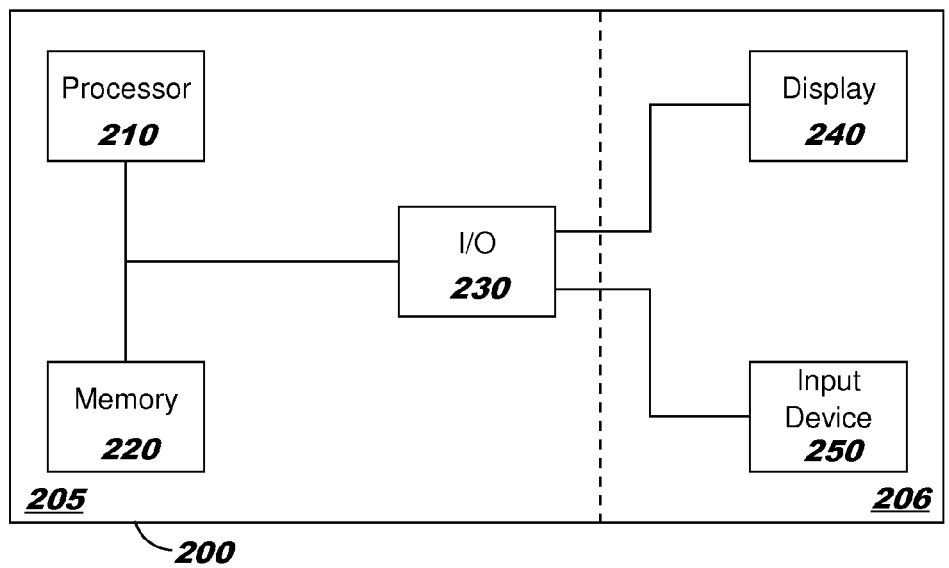
FIG. 2 is a block diagram of a data processing system in which various embodiments may be implemented.

FIG. 2 is a block diagram of a data processing system in which various embodiments may be implemented. Data processing system 200 is an example of a computer device, such as server 120, client 140, laptop 150, mobile phone 160, mask pump 170 or facility 180 in FIG. 1, in which computer usable program code or instructions implementing the processes may be located for the illustrative embodiments.

In the depicted example, data processing system 200 includes a CPU or central processing unit 210 which may contain one or more processors and may be implemented using one or more heterogeneous processor systems including a graphics processor. The depicted example also includes a memory 220 which may be used for storing instructions and data to be processed by CPU 210. Memory 220 may include a main memory composed of random access memory (RAM), read only memory (ROM), or other types of storage devices. Memory 210 could also include secondary storage devices such as a hard disk drive, DVD drive or other devices which may be internal or external to data processing system 200. An input output device (I/O) 230 is also shown in the depicted example for managing communications with various input devices and output devices. However, other examples could use the CPU to communicate directly with various input or output devices or use separate input and output controllers.

In the depicted example, a computer display 240 is shown for the data processing system to communicate with a user or another data processing system. Other types of output devices may be used such as an audio device. An input device 250 is also shown which may be a keyboard, mouse, a touch sensitive display, or other types of input devices.

Data processing system 200 is shown with an internal section 205 and an external section 206. Often input and output devices may be physically separate from but connected to the CPU and memory. However, that is often not the case with portable devices such as mobile phones.

An operating system may run on processor 210. The operating system coordinates and provides control of various components within data processing system 200 in FIG. 2. The operating system may be a commercially available operating system. An object oriented programming system may run in conjunction with the operating system and provides calls to the operating system from programs or applications executing on data processing system 200. Instructions for the operating system, the object-oriented programming system, and applications or programs may be located on secondary storage devices such a hard drive, and may be loaded into RAM for execution by processing unit 210.

The hardware in FIGS. 1-2 may vary depending on the implementation. Other internal hardware or peripheral devices, such as flash memory, equivalent non-volatile memory, or optical disk drives and the like, may be used in addition to or in place of the hardware depicted in FIGS. 1 and 2. In addition, the processes of the embodiments may be applied to a multiprocessor data processing system.

The depicted examples in FIGS. 1-2 and above-described examples are not meant to imply architectural limitations. For example, data processing system 200 may also be a mobile phone 160, tablet computer, laptop computer, or telephone device.

Figure 3:
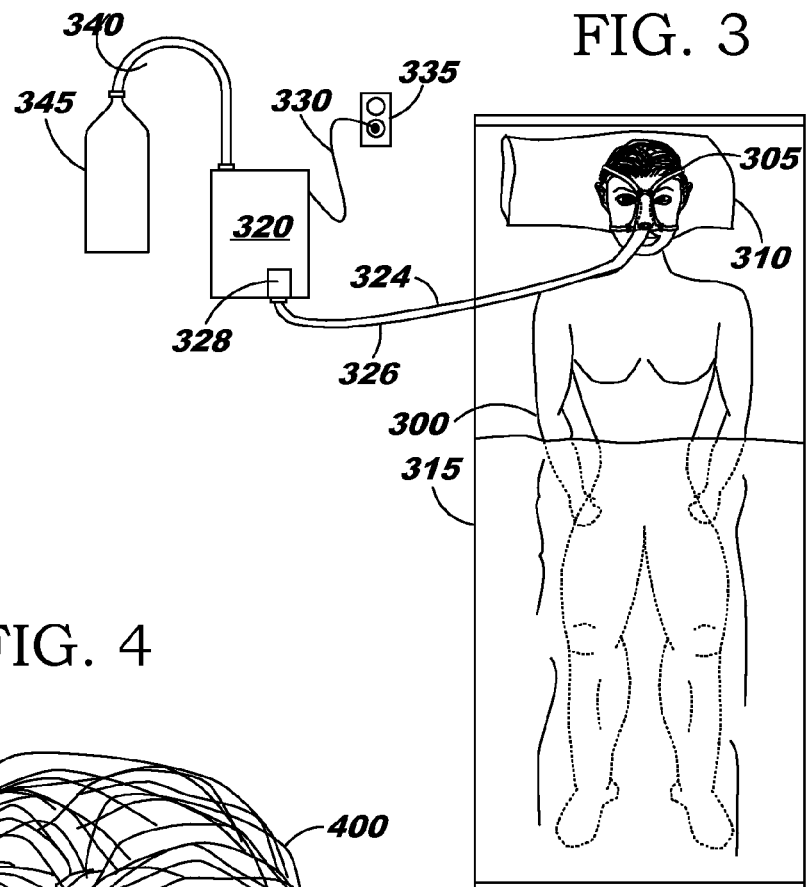
FIG. 3 is a diagram of a person using a positive airway pressure (PAP) system in which various embodiments may be implemented.

FIG. 3 is a diagram of a person using a positive airway pressure (PAP) system in which various embodiments may be implemented. There are several types of PAP systems in use for the treatment of sleep apnea. One type is a continuous positive airway pressure (CPAP) system where a continuous positive pressure is maintained. Another type is a bi-level positive airway pressure (BPAP) system where there are two different pressures, a higher one during inhalation and a lower one for exhalation. A BPAP system often uses an electronic circuit to monitor the person's breathing to synchronize pressure changes to that breathing.

A sleeping person 300 wearing a PAP mask 305 is laying on his or her back on a pillow 310 and bed 315. There are alternative sleep positions such as the person sleeping on his or her side, which may necessitate different pillow configurations. Mask 305 is connected to PAP machine 320 through an air hose 324 and wires 326. PAP machine 320 also has an air pressure sensor 328 to determine when a leak in the system, such as at mask 305, has occurred. Although air pressure sensor is shown at PAP machine 320, the sensor could be located anywhere along the air hose 324 or mask 305. Alternative mechanisms may be used to detect air leaks including microphone(s) located near or on the mask to listen for air leaks. Each air pressure sensor includes the capability to transmit a pressure value to a processing system such as by wire. Wires 326 may include power cables and communication cables. PAP machine 320 has an optional oxygen line to oxygen tank 345 and electrical wire 330 to electrical outlet 345.

PAP machine 320 may include a heater and/or humidifier or may be configured between the sleeping person and the PAP machine to warm and/or humidify the air being provided to the person through air hose 324. PAP machine 320 may be a standalone data processing system with a processor and software for managing the use of the various embodiments as described below. PAP machine 320 may also be coupled to a local computer system or to the internet by a wired or wireless connection. PAP mask may be one of a variety of types of masks that are nasal only, nasal and mouth, or even full face, each with a variety of shapes, configurations and possible straps to maintain a tight fit.

Figure 4:
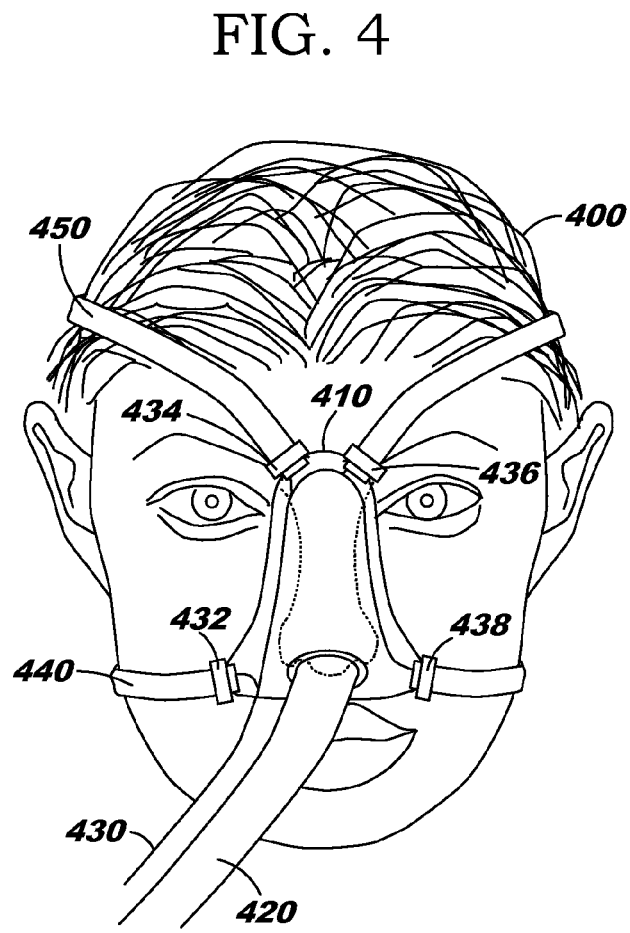
FIG. 4 is a diagram of a person wearing a PAP mask in accordance with a first embodiment.

FIG. 4 is a diagram of a person 400 wearing a PAP mask 410 in accordance with a first embodiment. In this example, a nasal only mask is shown although alternative embodiments could be implemented with a nasal and mouth mask or a full face mask. PAP mask 410 includes an air hose 420 and a set of power and control wiring 430. The power and control wiring may be attached to the air hose. Power and control wiring 430 is used to power and control the actions of tensioners 432, 434, 436 and 438. The tensioners are for the purpose of tightening or loosening straps 440 and 450. Each tensioner includes the capability to receive an adjustment value from a processing system such as by wire. Each tensioner may include a stepper motor which drives an axle attached to a strap. As the stepper motor turns the axle, the strap may be tightened or loosened. Alternative embodiments may use a pneumatic piston in-line with each strap or various types of hydraulic systems for tightening and loosening the straps. The adjustment value may be in terms of a distance value for a strap to be tightened or loosened or it may be a time value provided by the system knowing the physical properties of the stepper motor or other mechanism used to adjust the straps. Strap 440 extends behind the head below the ears and strap 450 extends behind the head above the ears. Straps 440 and 450 are used to hold the PAP mask in place without leakage. The mask may have a gel edge, some flaps or other alternative mechanisms to try to maintain a seal between the mask and face of the person while minimizing any skin irritation or other discomfort.

There are several areas where a leak may develop. One area is the nose bridge where there may be a leak between tensioners 434 and 436. A second area is by the cheekbones one either side of the face between tensioners 432 and 434 or between tensioners 436 and 438. A third area is below the nose between tensioners 438 and 432.

There are several causes for leaks. One cause may be the person shifting in his or her sleep where the mask may be knocked lose or misadjusted by the pillow or a hand of the sleeping person. Another cause may be a change in bedroom temperature which may change the stiffness of the mask. A further cause may be from the muscles of the face relaxing as the person falls asleep. In any case, such a leak can disrupt the effectiveness of the PAP mask, thereby creating health issues for the person wearing the mask.

In operation, if PAP machine 320 detects an air leak with air pressure sensor 328, the tensioners 432, 434, 436 and 438 may all be tightened to attempt to seal the mask and prevent the leak. However, that level of tightness may cause excessive chaffing or other issues with the person, disturbing sleep. Once the mask is sealed and the air leak stopped, various tensioners may be loosened in sequence to determine the source of the leak. For example, tensioners 432 and 434 may be loosened slightly to determine if the leak is on the person right cheekbone area. If no air leak develops, then additional tensioners may be loosened and tightened to determine the source of the air leak. These processes are described with reference to the flowchart below.

Figure 5:
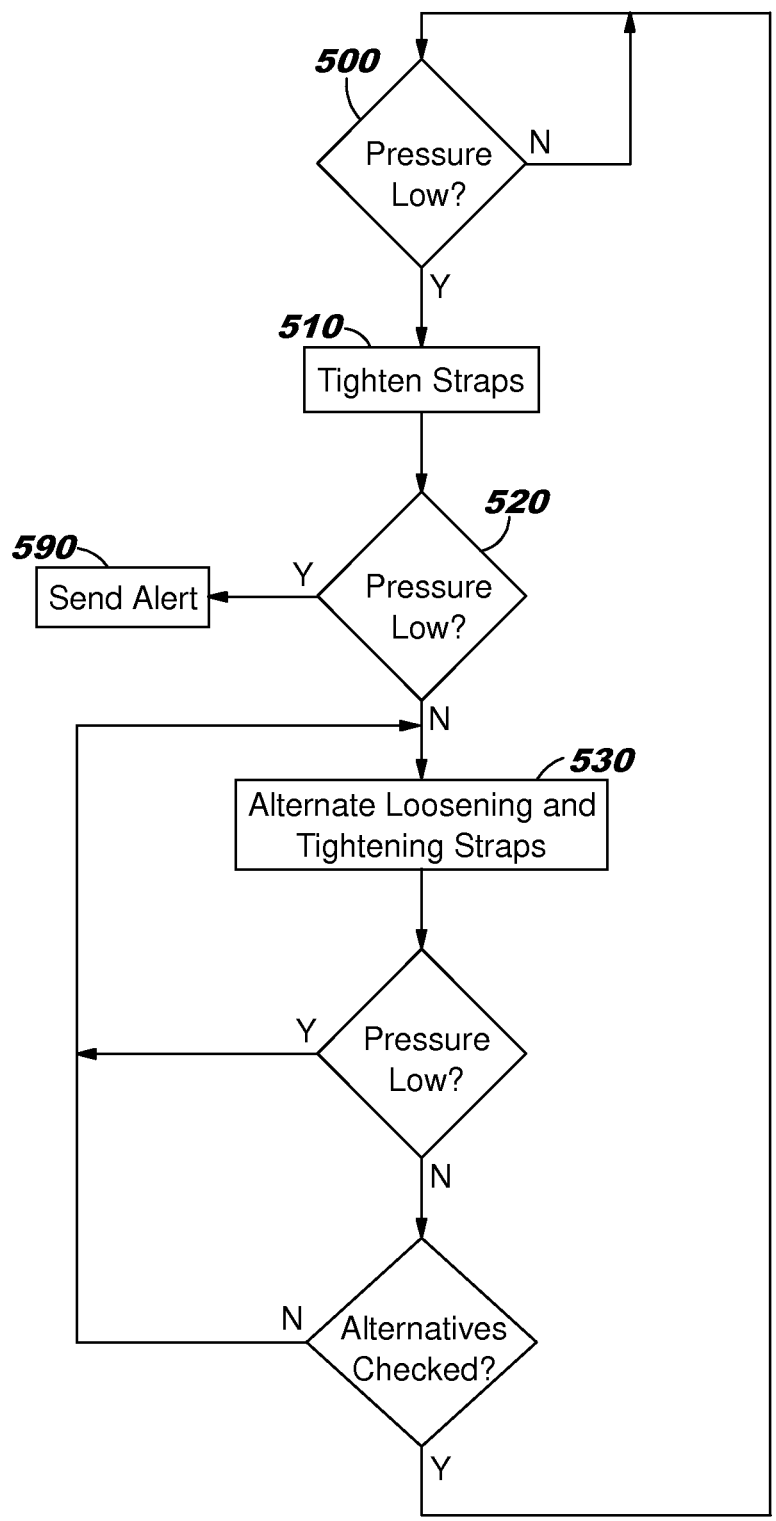
FIG. 5 is a flowchart of the operation of the PAP system in accordance with the first embodiment.

FIG. 5 is a flowchart of the operation of the PAP system in accordance with the first embodiment. Alternative approaches may be used to implement these embodiments as well as other alternative embodiments.

In a first step 500, a sensor such as air pressure sensor 328 may detect low pressure due to a leak in the PAP mask. The air pressure sensor includes the capability to transmit a pressure value to a processing system such as by wire. The leak may be caused by a variety of factors described above with reference to the first embodiment. Once detected, then in step 510 all the straps are tightened using the tensioners to try to seal the mask. Each tensioner includes the capability to receive an adjustment value from a processing system such as by wire. The straps are tightened by a preset amount that may be modified by software changes in the PAP system. There may also be preset limits as to how much each strap may be tightened to avoid excessive pressure on the face of the patient. These preset amounts may be set at the factory and modified by a medical professional or other person with access to software running the PAP system. In step 520, it is determined whether a low pressure condition continues or whether tightening all the straps sealed the leak. If low pressure indicates a continuing leak is detected, then processing continues to step 590 where an alert may be sent. The alert may be a simple audible alarm to awaken the person wearing the mask and inform that individual that the mask needs to be sealed manually. The alert may also be an electronic signal sent to a caretaker or medical professional that the mask is no longer sealed. That electronic signal may be a wired or wireless signal to a local computer system or to a remote system through the internet. The signal may be sent immediately upon the low pressure condition or may be sent at a later time. A medical processional may review this and other electronic signals to determine if changes need to be made to the mask, whether the mask wearer needs additional training or whether other actions need to be taken If no low pressure condition is detected in step 520, then processing continues to step 530 where various straps may be loosened or tightened by the tensioners to reduce the amount of strap tension for reducing skin irritation and patient discomfort while maintaining a sealed mask. Each time various straps are loosened or tightened, the air pressure sensor for the system will determine if a low pressure condition has reoccurred indicating a leak has reoccurred. If yes, then processing returns to step 530 to try other combinations of loosening or tightening of the straps. If not, then in step 550 it is determined whether a sufficient number of alternatives for loosening or tightening of straps has occurred to determine the area of the leak and to reduce the total pressure on the patients face while maintaining a seal. If yes, then processing returns to step 500. If not, then processing returns to step 530 to continue testing the tightening and loosening of various straps.

Even though a seal was maintained in steps 530 through 550, the system may still provide data to a local or remote system for analysis of this type of data over time. This could allow a medical professional to determine whether certain actions may be taken to reduce the likelihood of future leaks.

Figure 6:
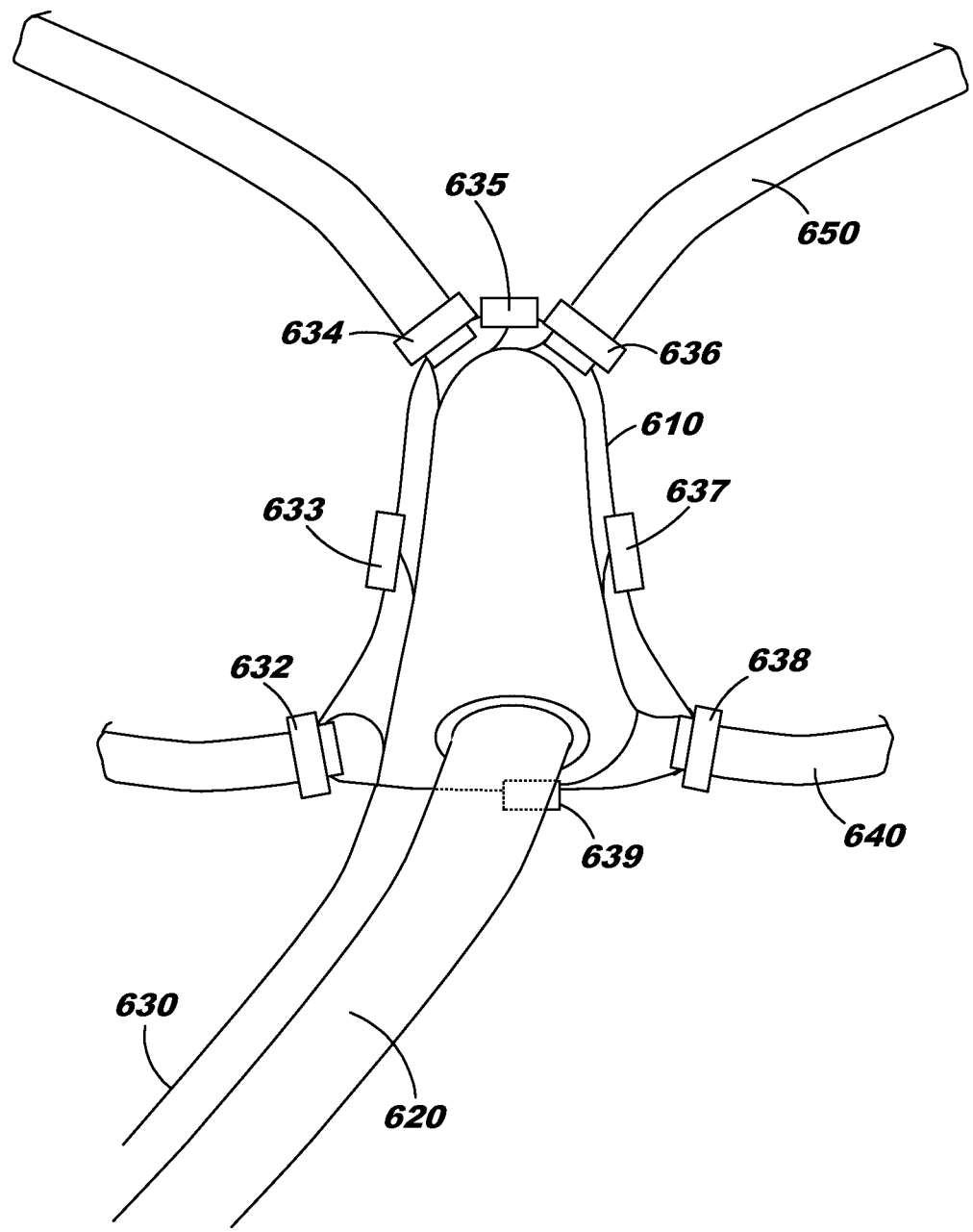
FIG. 6 is a diagram of a PAP mask in accordance with a second embodiment.

FIG. 6 is a diagram of a PAP mask 610 in accordance with a second embodiment. In this example, a nasal only mask is shown although alternative embodiments could be implemented with a nasal and mouth mask or a full face mask. PAP mask 610 includes an air hose 620 and a set of power and control wiring 630. The power and control wiring may be attached to the air hose. Power and control wiring 630 is used to power and control the actions of tensioners 632, 634, 636 and 638 as well as force pressure sensors 633, 635, 637 and 639. Each force pressure sensor includes the capability to transmit a pressure value to a processing system such as by wire. The tensioners are for the purpose of tightening or loosening straps 640 and 650. Each tensioner includes the capability to receive an adjustment value from a processing system such as by wire. Each tensioner may include a stepper motor which drives an axle attached to a strap. As the stepper motor turns the axle, the strap may be tightened or loosened. Alternative embodiments may use a pneumatic piston in-line with each strap or various types of hydraulic systems for tightening and loosening the straps.

The force pressure sensors are for determining the pressure applied at potential air leakage points on the mask. The force pressure sensors may be piezoresistive based and may fully extend around the mask. If a segmented gel tube is used to help seal the mask, the pressure at each segment of the tube may be measured using hydraulic pressure sensors. Strap 640 extends behind the head below the ears and strap 650 extends behind the head above the ears. Straps 640 and 650 are used to hold the PAP mask in place without leakage. The mask may have a gel edge, some flaps or other alternative mechanisms to try to maintain a seal between the mask and face of the person while minimizing any skin irritation or other discomfort.

There are several areas where a leak may develop. One area is the nose bridge where there may be a leak between tensioners 634 and 636 at force pressure sensor 635. A second area is by the cheekbones one either side of the face between tensioners 632 and 634 at force pressure sensor 633 or between tensioners 636 and 638 at force pressure sensor 637. A third area is below the nose between tensioners 638 and 632 at force pressure sensor 639.

In operation, if PAP machine 320 detects an air leak with air pressure sensor 328, the tensioners 532, 634, 636 and 638 may all be tightened to attempt to seal the mask and prevent the leak. However, that level of tightness may cause excessive chaffing or other issues with the person, disturbing sleep. Once the mask is sealed and the air leak stopped, various tensioners may be loosened in sequence based on the input of the various force pressure sensors to determine the source of the leak. For example, tensioners 632 and 634 may be loosened slightly to determine if the leak is on the person right cheekbone area. If no air leak develops, then additional tensioners may be loosened and tightened to determine the source of the air leak. Also in operation, if the tightness of the mask is determined to be excessive in certain areas even though no leak has occurred, then certain tensioners may be loosened to relieve that pressure. The mask is then checked for air leaks by the air pressure sensor. If a leak is found, then the tensioners may be retightened. These processes are described with reference to the flowchart below.

Figure 7:
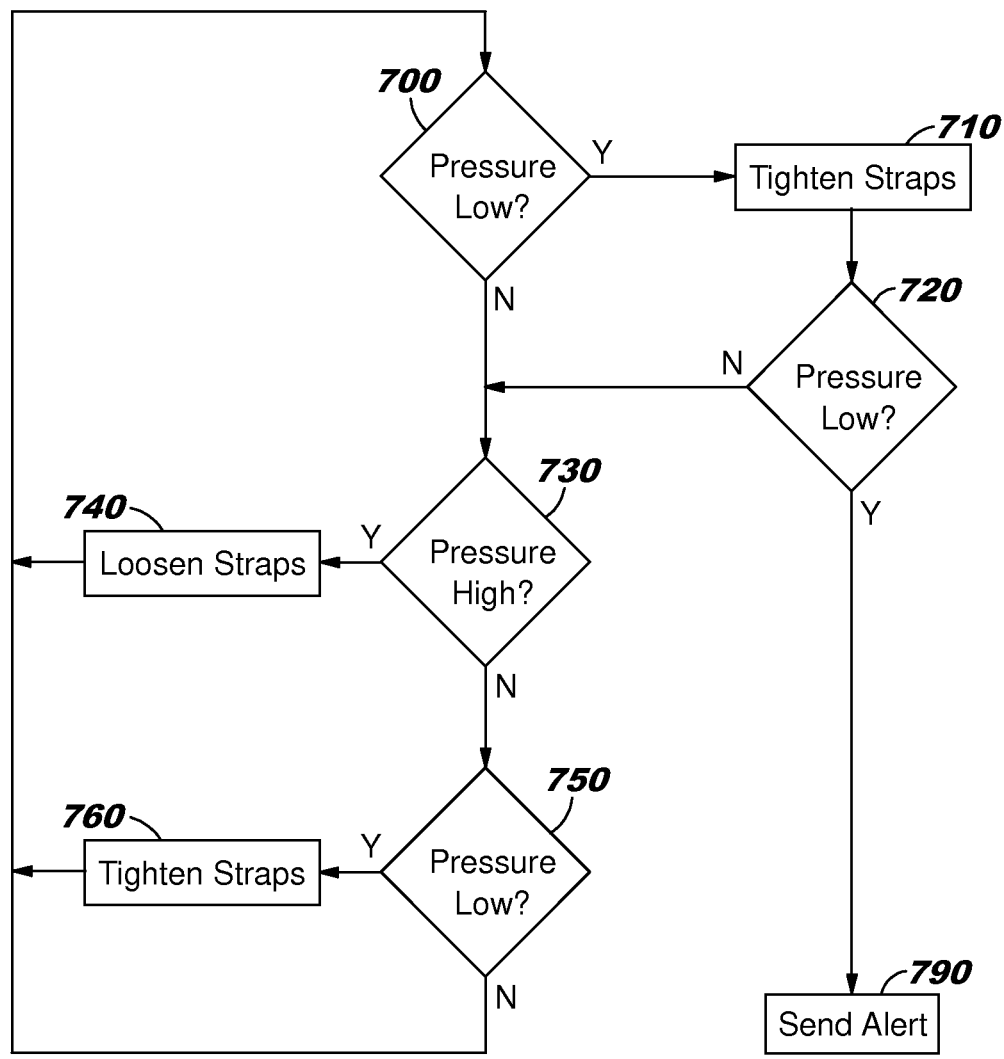
FIG. 7 is a flowchart of the operation of the PAP system in accordance with the second embodiment.

FIG. 7 is a flowchart of the operation of the PAP system in accordance with the second embodiment. Alternative approaches may be used to implement these embodiments as well as other alternative embodiments.

In a first step 700, a sensor such as air pressure sensor 328 may detect a low pressure condition indicating a leak in the PAP mask. The leak may be caused by a variety of factors described above with reference to the second embodiment. Once detected, then in step 710 straps are tightened using the tensioners to try to seal the mask. The amount that each strap is tightened may be modified based on input from the force pressure sensors. That is, the straps near force pressure sensors detecting greater force pressure may be tightened less than those straps near force pressure sensors detecting less force pressure. This type of condition may occur when the person sleeping is laying on one side torqueing the PAP mask. In step 720, it is determined whether a low pressure condition continues or whether tightening the straps sealed the leak. If low pressure indicates that a continuing leak is detected, then processing continues to step 790 where an alert may be sent. The alert may be a simple audible alarm to awaken the person wearing the mask and inform that individual that the mask needs to be sealed manually. The alert may also be an electronic signal sent to a caretaker or medical professional that the mask is no longer sealed. That electronic signal may be a wired or wireless signal to a local computer system or to a remote system through the internet. The signal may be sent immediately upon the leak condition or may be sent at a later time. A medical processional may review this and other electronic signals to determine if changes need to be made to the mask, whether the mask wearer needs additional training or whether other actions need to be taken If no low pressure condition is detected in step 700 or in step 720, then processing continues to step 730. In step 730 it is determined if any of the force pressure sensors are measuring a force higher than desired to prevent skin irritation and patient discomfort. If yes, then processing continues to step 740 where straps near those force sensors are loosened. Processing would then return to step 700 to determine if this action created any leaks. If no in step 730, then processing continues to step 750. In step 750, it is determined if any of the force pressure sensors are measuring a force low enough to indicate a leak may be forthcoming shortly. If yes, then processing continues to step 760 where straps near those force pressure sensors are tightened. Once the loose straps are tightened in step 760 or if no straps were determined to be lose in step 750, then processing returns to step 700.

Even those a seal was maintained throughout the above described steps, the system may still provide data to a local or remote system for analysis of this type of data over time. This could allow a medical professional to determine whether certain actions may be taken to reduce the likelihood of future leaks.

Alternative embodiments could include other types of masks which require a seal be maintained. Examples include positive air pressure masks used by emergency personnel in hazmat conditions, researchers in biological laboratories, or other types of masks used by governmental, commercial or private personnel which may be exposed to chemical, biological or other types of undesirable contaminants.

The invention can take the form of an entirely software embodiment, or an embodiment containing both hardware and software elements. In a preferred embodiment, the invention is implemented in software or program code, which includes but is not limited to firmware, resident software, and microcode.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM), or Flash memory, an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Further, a computer storage medium may contain or store a computer-readable program code such that when the computer-readable program code is executed on a computer, the execution of this computer-readable program code causes the computer to transmit another computer-readable program code over a communications link. This communications link may use a medium that is, for example without limitation, physical or wireless.

A data processing system suitable for storing and/or executing program code will include at least one processor coupled directly or indirectly to memory elements through a system bus. The memory elements can include local memory employed during actual execution of the program code, bulk storage media, and cache memories, which provide temporary storage of at least some program code in order to reduce the number of times code must be retrieved from bulk storage media during execution.

A data processing system may act as a server data processing system or a client data processing system. Server and client data processing systems may include data storage media that are computer usable, such as being computer readable. A data storage medium associated with a server data processing system may contain computer usable code such as software for managing the performance of an active mask strap tensioning system or for downloading performance data to a historical database. A client data processing system may download that computer usable code, such as for storing on a data storage medium associated with the client data processing system, or for using in the client data processing system. The server data processing system may similarly upload computer usable code from the client data processing system such as a content source. The computer usable code resulting from a computer usable program product embodiment of the illustrative embodiments may be uploaded or downloaded using server and client data processing systems in this manner.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to explain the principles of the invention, the practical application, and to enable others of ordinary skill in the art to understand the invention for various embodiments with various modifications as are suited to the particular use contemplated.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method for managing a set of active straps for a positive airway pressure (PAP) mask, the method comprising:
   detecting a mask air pressure value of an air volume contained by the PAP mask to determine whether an air leak has occurred;
   detecting a force pressure value measured between the PAP mask and a face with a force pressure sensor;
   responsive to detecting an air leak, analyzing the force pressure value with a processor for identifying an adjustment of the set of active straps; and
   performing the identified adjustment with the set of active straps.

2. The method of claim 1 wherein the identified adjustment is a preset adjustment that is modified based on the force pressure value.

3. The method of claim 2 wherein the identified adjustment is limited by a preset limit.

4. The method of claim 1 wherein multiple force pressure sensors measure force pressure values between the PAP mask and a portion of the face.

5. The method of claim 4 wherein the identified adjustment is a tightening of at least one of the set of active straps based on the force pressure values.

6. The method of claim 1 further comprising responsive to not detecting an air leak, utilizing the force pressure value to identify a second adjustment of the set of active straps.

7. The method of claim 1 wherein the pressure value and the identified adjustment are sent to a data processing system for tracking and analysis; and wherein the analysis is utilized to modify adjustments to reduce the likelihood of future air leaks.

8. The method of claim 1 further comprising a second force pressure sensor measuring a second force pressure value between the PAP mask and a face;
- wherein analyzing includes analyzing the air pressure value and the second force pressure value with the processor for identifying the adjustment of the set of active straps;
- wherein the adjustment is a tightening of at least one strap and the loosening of at least one strap; and
- wherein the force pressure value and the identified adjustment are sent to a data processing system for tracking and analysis; and
- wherein the analysis is utilized to modify adjustments to reduce the likelihood of future air leaks.

9. The method of claim 1 wherein the identified adjustment is a tightening of at least one of the set of active straps based on the force pressure values.

10. The method of claim 1 wherein the identified adjustment is a loosening of at least one of the set of active straps based on the force pressure values.

* * * * *